United States Patent [19]
Donohue et al.

[11] Patent Number: 4,740,080
[45] Date of Patent: Apr. 26, 1988

[54] ANALOG TO DIGITAL CONVERTER FOR FLUID ANALYZING APPARATUS

[75] Inventors: Joseph P. Donohue, Waukegan; Mitchell S. Budniak, Skokie, both of Ill.

[73] Assignee: Abbott Laboratories, North Chicago, Ill.

[21] Appl. No.: 714,310

[22] Filed: Mar. 21, 1985

[51] Int. Cl.⁴ .................................................. G01J 3/36
[52] U.S. Cl. ..................................... 356/326; 250/564; 356/39
[58] Field of Search .................... 356/39, 40, 306, 313, 356/326, 328, 41, 320, 407, 409, 411; 250/564, 565

[56] References Cited

U.S. PATENT DOCUMENTS 2,446,874  8/1948  Geffner et al. ....................... 356/306
3,627,421 12/1971  Harley et al. ....................... 356/313

Primary Examiner—F. L. Evans
Attorney, Agent, or Firm—Donald L. Corneglio; Martin L. Katz; Rodney A. Daniel

[57] ABSTRACT

A device for producing a digital representation of an analog signal in apparatus for use in analyzing samples of biological material. The apparatus conducts such analysis by optical techniques, whereby an analog signal is generated which corresponds to the strength of a light component impinging a light responsive element.

7 Claims, 1 Drawing Sheet

ANALOG TO DIGITAL CONVERTER FOR FLUID ANALYZING APPARATUS

BACKGROUND OF THE INVENTION

This invention relates to apparatus for analyzing the constituent parts of a fluid such as blood serum. More particularly, this invention relates to blood serum analysis apparatus which ascertains the constituent parts of a blood serum sample by optical analysis at an apparatus testing station.

Apparatus of the type described conventionally utilizes a first probe for aspirating a blood serum sample and depositing such sample in a transparent laboratory vessel known as a cuvette located at the apparatus testing station. A second probe is then used to aspirate a reagent which is typically transported to the cuvette where it is contacted with the blood serum sample previously deposited therein. In accordance with techniques well known in the art, a particular reagent will bind to a predetermined constituent part of the blood serum sample, thereby isolating that part in the cuvette for subsequent optical analysis. If other parts required analysis, different reagents are ordinarily utilized.

After a particular constituent part of the blood serum sample has been isolated by contacting the sample with a particular reagent, the part may be optically analyzed by applying a beam of light to the cuvette in a well known manner. The isolated constituent part of the blood serum sample in the cuvette absorbs some of this light at different wavelengths, depending upon the characteristics of the sample. An altered light beam thus emerges from the sample under analysis, and typically passes through an optical medium which causes it to be diffracted into a plurality of discrete light components. These different light components, each characterized by a different wavelength, propagate at predetermined paths relative to the optical medium through which they pass.

Conventional optical analysis apparatus takes advantage of the fact that these discrete light components propagate at predetermined positional relationships by locating light responsive circuit elements at focusing positions along various ones of these predetermined paths. These circuit elements typically produce an electrical current signal that is proportional to the intensity of the light impinging thereon. Thus, if one such circuit element is positioned to be impinged by a light component characterized by a first wavelength, it will produce a relatively strong current signal if the relative intensity of that component is strong. On the other hand, if an adjacent circuit element is positioned to be impinged by a different light component characterized by a second wavelength, it will produce a relatively weak current signal if the relative intensity of that component is weak.

The current signals produced by such circuit elements in analog form are then electrically manipulated in a well known manner to generate a digital signal corresponding to the absorptance of the light applied to the sample isolated in the cuvette. This signal is indicative of the characteristics of that sample.

Though optical fluid analyzers of the type described have been used successfully, they are subject to certain drawbacks and deficiencies. For example, it would be highly desirable to provide improved circuitry for electrically manipulating the analog current signals produced by the light responsive circuit elements to develop the digital information corresponding to the absorptance of the light applied to the blood serum sample under analysis.

It is the object of this invention to provide such circuitry.

SUMMARY OF THE INVENTION

The improved circuitry for converting an analog current signal into digital information useful in ascertaining the absorptance of a sample of biological material includes a pair of light responsive elements adapted to be impinged, respectively, by a discrete light components characterized by different wavelengths, each light responsive element developing a current signal corresponding to the strength of the impinging light component. Storage means, coupled to each light responsive element, stores a charge corresponding to the strength of the current signal so developed, and a pair of circuit means, coupled to the respective storage means causes such storage means to discharge until the charge stored therein is substantially dissipated. Such discharge occurs in periodic increments, the number of increments corresponding to the strength of the current signal. Since this number can be expressed in digital terms, the analog current signal is effectively converted into digital form.

In another aspect of the invention there is disclosed a method for producing a digital representation of an analog signal for use in the analysis of a sample of biological material. The method comprises the steps of producing first and second analog signals each having a strength useful in the analysis of such material, storing a pair of electrical signal corresponding to the strengths of the first and second analog signals in respective electrical storage means, causing the electrical signals to be dissipated from the corresponding storage means in periodic increments, and generating a first and a second number of pulses substantially corresponding to the corresponding number of increments. The first and second numbers of such pulses is a digital representation of the strengths of the analog signals, and can be counted by any appropriate circuitry.

BRIEF DESCRIPTION OF THE DRAWINGS

An exemplary embodiment of the invention summarized above is illustrated in the accompanying drawings wherein.

DETAILED DESCRIPTION OF EXEMPLARY EMBODIMENTS OF THE INVENTION

Figure 1:
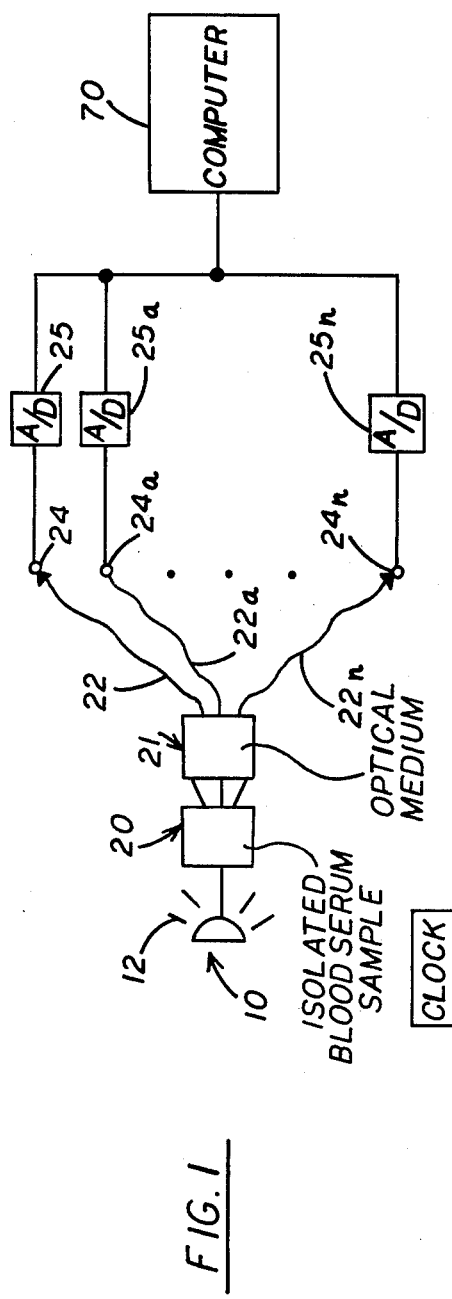
FIG. 1 is a schematic diagram of the means for generating an analog signal useful in this invention.

Referring now to FIG. 1 there is illustrated in schematic form a light source 10 producing a beam of light 12. Though represented in schematic form, it will be understood by those skilled in the art that source 10 includes all necessary optical elements such as filters, light passages, etc. to provide the beam of light 12 that is required to permit optical analysis to proceed.

Light 12 is directed from source 10 to an isolated part 20 of the blood serum sample to be analyzed. Part 20 is ordinarily contained in a transparent cuvette (not shown) through which light 12 is directed. In accordance with well known operation, some of light 12 is absorbed by part 20. Accordingly, an altered portion of the beam of light originating from source 10 emerges from part 20 and is passed through a conventional optical medium 21 where it is diffracted to form a plurality of discrete light components 22, 22a ... 22n, each characterized by a different wavelength.

The propagation paths of light components 22, 22a ... 22n relative to optical medium 21 is determined by well known and well understood physical laws. Accordingly, predetermined focal positions 24, 24a ... 24n, are defined respectively by the propagation paths of light components 22, 22a ... 24n. Thus, by locating a light responsive circuit element, such as a conventional photo diode, at each of positions 24, 24a ... 24n, an electrical current signal, having a parameter (such as current amplitude) corresponding to the intensity of the light impinging at any one of positions 24, 24a ... 24n can be generated.

The electrical current signals generated by properly positioned light responsive elements are passed to A to D convertors 25, 25a ... 25n. These converters convert the analog information associated with the corresponding electrical current signals into digital information in a manner explained in greater detail in connection with the description of FIG. 2. In accordance with well-known blood serum analysis techniques, the logarithm of the ratio of two adjacent signals is ascertained by computer means 70. One particularly desirable method for determining this ratio is disclosed in co-pending U.S. application Ser. No. 06/620,059 filed on June 13, 1984, now abandoned. The teachings of this application are incorporated herein by reference.

Figure 2:
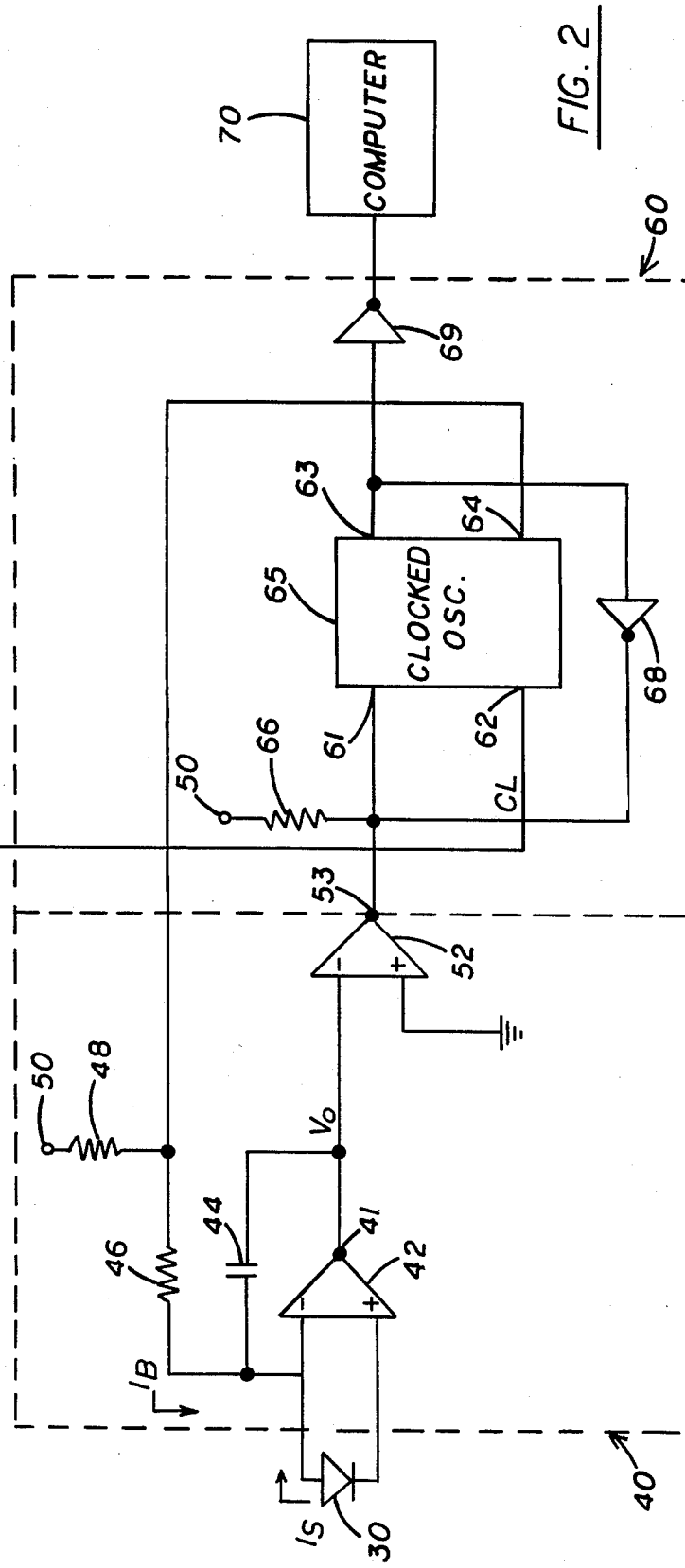
FIG. 2 is a schematic circuit diagram of the components used for producing a digital representation of the analog signal generated by means such as the type illustrated schematically in FIG. 1.

A properly positioned light responsive element and related circuitry for generating electrical information signals having a parameter corresponding to the intensity of the light impinging at any one of positions 24, 24a ... 24n is represented by photo diode 30 in FIG. 2. Photo diode 30 conventionally produces an analog signal in the form of a current signal having a magnitude corresponding to the strength of the impinging light component.

Referring now to FIG. 2, photo diode 30 is shown to be coupled to a block 40, sometimes referred to generally herein as electrical storage means. Electrical storage means 40 includes an integrator 42, having positive and negative inputs coupled, respectively, to the cathode and anode of diode 30. A capacitor 44 is coupled between the negative input of integrator 42, and the output thereof identified by reference numeral 41. The negative input of integrator 42 is also coupled through a resistor 46 and a resistor 48 to a supply voltage 50. Diode 30 produces an electrical current signal $I_S$ which is applied to the negative input terminal of integrator 42. A bias signal $I_B$, resulting from the application of supply voltage 50 to resistor 46 is also applied to the negative input terminal of integrator 42.

Integrator 42 operates in a conventional manner to produce an integrated signal Vo at its output 41. Integrated signal Vo can be represented by the equation $-1/c \int I_S + I_B \, dt$, where c represents the capacitance of capacitor 44.

The integrated signal Vo is applied to the negative input terminal of a voltage comparator 52. The positive input terminal of comparator 52 is coupled to a reference potential such as ground. Comparator 52 is an open collector device whereby a relative low state appears at its output 53 when the signal at its positive input terminal is less than the signal at its negative input terminal, and a relative high state appears at output 53 when the signal at its positive input terminal is greater than the signal at its negative input terminal.

Output 53 of comparator 52 is applied to a block sometimes referred to herein as circuit means 60. Circuit means 60 includes a clocked oscillator 65—device no. 74HC175 in this exemplary embodiment. Oscillator 65 has an input 61 coupled to output 53 of comparator 52. Input 61 is also coupled through a resistor 66 to supply voltage 50. Oscillator 65 further includes a clocked input 62 adapted to receive periodic clock pulses CL from a clock. In this exemplary embodiment the clock pulses are applied to clock input 62 at a 2.6 MHz rate, though this rate should not be construed as limitative.

Oscillator 65 also has a pair of outputs 63, 64, presenting opposite states. For example, if output 63 presents a relatively high state, output 64 presents a relatively low state, and vice versa. Output 63 of oscillator 65 is passed through an inverter 68 to input 61.

When oscillator 65 receives a relatively high signal at its input 61, the state of its outputs 63, 64 will change with the next clock pulse applied at clock input 62. For example, if the states at outputs 63, 64 are high and low, respectively, these states will reverse at the next clock pulse when the signal at input 61 changes from low to high. Since output 63 is coupled to input 61 through inverter 68, however, outputs 63, 64 will periodically change states, substantially as long as the output 53 of comparator 52 remains relatively high. In this way a train of pulses is generated at output 63 at substantially one half the clock pulse rate.

Output 64 of oscillator 65 is coupled to the junction of resistors 46, 48. This, in turn, provides a path from capacitor 44 to output 64 via resistor 46. Since output 64 displays the opposite state as output 63, a relatively low pulse will appear at output 64 at substantially one-half the clock pulse rate. Each time output 64 becomes relatively low, capacitor 44 dissipates an incremental amount of charge through resistor 46. As such the periodic transitions at output 64 cause the charge stored on capacitor 44 to discharge in periodic increments.

Output 63 of oscillator 65 is also coupled to computer means via a buffer 69. Buffer 69 serves to isolate circuit means 60 from the remainder of the circuitry thereby preventing spurious signals and the like from interfering with circuit operation. Computer means 70 operates to count the number of pulses produced at output 63 of oscillator 65. Moreover, upon counting the pulses associated with signals resulting from two adjacent photo diodes of the type represented by photo diode 30, computer means 70 can further develop a signal corresponding to the logarithmic ratio indicative of the absorptance of the sample being analyzed.

The operation of the circuitry shown in FIG. 2 can now be described. As previously explained, current $I_S$ generated by diode 30, and current $I_B$ from supply voltage 50, is applied to capacitor 44. A charge corresponding to the sum of those current signals is thus stored by that capacitor. Since current signal $I_S$ is indicative of the strength of the light component impinging diode 30, the charge on capacitor 44 corresponds to the strength of that component. Integrator 42 then produces an integrated signal Vo which is represented by the equation $Vo = -1/c \int I_S + I_B \, dt$.

The integrated signal Vo is applied to the negative terminal of comparator 52, causing the output thereof to change from a relatively low to a relatively high state.

This change causes a train of pulses to be produced at output 63 of oscillator 65 at substantially one-half the clock pulse rate so long as the output 53 of comparator 52 remains relatively high. The production of each such pulse causes capacitor 44 to be incrementally discharged until its charge has been dissipated. When this occurs, the signal Vo applied to the negative terminal of comparator 52 is dramatically reduced, whereby the output 63 returns to a relatively low state. This prevents oscillator 65 from producing additional pulses at output 63.

It should thus be apparent that oscillator 65 produces pulses at its output 63 until the charge on capacitor 44 is substantially dissipated. The number of pulses so produced corresponds to the strength of the current signal $I_S$, an analog signal corresponding to the strength of the light component impinging diode 30. This number is a digital representation of the strength of that light component. By counting those pulses, this representation can, of course, be represented in digital terms if desired.

What has been described is a novel device for representing an analog signal in digital form for use in apparatus for analyzing samples of biological material. Though the embodiment disclosed herein is preferred, numerous modifications and variations which do not part from the true scope of the invention will be apparent to those skilled in the art. All such modifications and variations are intended to be covered by the appended claims.

We claim:

1. A device for analyzing a biological material by exposing said material to light and passing said light through an optical medium where it is converted into a plurality of discrete light components characterized by different wavelengths comprising:

a pair of light responsive elements adapted to be impinged by different ones of said light components, each of said light responsive elements developing a current signal corresponding to the strength of the impinging light component;

first storage means including an integrator with an input coupled to one of said light responsive elements; a capacitor coupled across said integrator for storing a first charge corresponding to the strength of the light component impinging said one of said light responsive elements; and a comparator having an input coupled to said integrator, producing a first output signal when said capacitor is substantially charged, and a second output signal when said capacitor is substantially discharged;

second storage means including an integrator with an input coupled to another of said light responsive elements; a capacitor coupled across said integrator for storing a second charge corresponding to the strength of the light component impinging said other of said light responsive elements; and a comparator having an input coupled to said integrator, producing a first output signal when said capacitor is substantially charged, and a second output signal when said capacitor is substantially discharged;

first circuit means, including cyclable means having a signal input coupled to said comparator of said first storage means, and a return output coupled to the capacitor of said first storage means to apply a first number of periodic reproducible discharge pulses to the capacitor such that each pulse discharges a determinable reproducible amount of said first charge; said first circuit means causing said capacitor of said first storage means to discharge said first charge in a first number of periodic increments until said first charge is substantially dissipated, whereby the first number of increments corresponds to the strength of one of said current signals;

second circuit means, including cyclable means having a signal input coupled to said comparator of said second storage means, and a return output coupled to the capacitor of said second storage means to apply a second number of periodic reproducible discharge pulses to the capacitor such that each pulse discharges a determinable reproducible amount of said second charge; said second circuit means causing said capacitor of said second storage means to discharge said second charge in a second number of periodic increments until said second charge is substantially dissipated, whereby the second number of increments corresponds to the strength of another one of said current signals; and computation means, coupled to said first and second circuit means, for receiving signals corresponding to said first and second numbers, and using said signals to develop an output indicative of the analysis of said material.

2. The device defined in claim 1 wherein said first and second circuit means each produce a number of pulses corresponding, respectively, to said first and second number of increments.

3. The device defined in claim 1 wherein each of said cyclable means has a signal output coupled to said signal input, said signal output periodically changing from a first state to a second state when a corresponding first output signal is received at a corresponding signal input, whereby one of said pulses is produced each time said periodic change from said first state to said second state occurs.

4. The device defined in claim 3 wherein each of said storage means undergoes an incremental discharge when the signal at a corresponding signal output of said cyclable means changes from said first state to said second state.

5. The device defined in claim 4 wherein each of said storage means further includes a resistor coupled between a corresponding capacitor in said storage means, and corresponding cyclable means in said circuit means providing a discharge path for said capacitor.

6. The device defined in claim 4 wherein each of said cyclable means comprises a bistable device having a clock input adapted to receive clock signals, whereby said change from said first state to said second state occurs upon receipt of a clock signal.

7. A device for analyzing a biological material by exposing said material to light and passing said light through an optical medium where it is converted into a plurality of discrete light components characterized by different wavelengths comprising:

at least two light responsive elements adapted to be impinged by different ones of said light components, each of said light responsive elements developing a current signal corresponding to the strength of the impinging light component;

first storage means comprising an integrator with an input coupled to one of said light responsive elements; a capacitor coupled across said integrator for storing a first charge corresponding to the strength of the light component impinging said one of said light responsive elements; and a comparator having an input coupled to said integrator, producing a first output signal indicative of the state of charge of the capacitor;

second storage means comprising an integrator with an input coupled to another of said light responsive elements; a capacitor coupled across said integrator for storing a second charge corresponding to the strength of the light component impinging said other of said light responsive elements; and a comparator having an input coupled to said integrator, producing a first output signal indicative of the state of charge of the capacitor;

means for generating a periodic clock signal;

first circuit means comprising digital cyclable means having a clock signal input adapted to receive the clock signal, a signal input coupled to said comparator of said first storage means, and a digital output coupled to the capacitor of said first storage means to apply to said capacitor a series of periodic digital waveforms, each waveform of predetermined voltage, current and duration, to discharge said first charge in a first number of periodic discharges, whereby each discharge is synchronized with the clock signal and the first number of increments corresponds to the strength of one of said current signals;

second circuit means comprising digital cyclable means having a clock signal input adapted to receive the clock signal, a signal input coupled to said comparator of said second storage means, and a digital output coupled to the capacitor of said second storage means to apply to said capacitor a series of periodic digital waveforms, each waveform of predetermined voltage, current and duration, to discharge said second charge in a second number of periodic discharges, whereby each discharge is synchronized with the clock signal and the second number of increments corresponds to the strength of the other one of said current signals; and computation means, coupled to said first and second circuit means, for receiving signals corresponding to said first and second numbers, and using said signals to develop an output indicative of the analysis of said material.

* * * * *